United States Patent
Nagayoshi et al.

(10) Patent No.: US 7,068,368 B1
(45) Date of Patent: Jun. 27, 2006

(54) TWO-SIDE MULTIPLE LAMP ONLINE INNER PART INSPECTION APPARATUS

(75) Inventors: Atsuhiro Nagayoshi, Shizuoka (JP); Hiromu Maeda, Shizuoka (JP)

(73) Assignee: Kabushikikaisha Kajitsuhihakaihinshitsukenkyujo, Shizuoka (JP)

( * ) Notice: Subject to any disclaimer, the term of this patent is extended or adjusted under 35 U.S.C. 154(b) by 608 days.

(21) Appl. No.: 10/088,889

(22) PCT Filed: Sep. 21, 2000

(86) PCT No.: PCT/JP00/06477

§ 371 (c)(1),
(2), (4) Date: Mar. 22, 2002

(87) PCT Pub. No.: WO01/22062

PCT Pub. Date: Mar. 29, 2001

(30) Foreign Application Priority Data

Sep. 24, 1999 (JP) .......................................... 11-271151

(51) Int. Cl.
*G01J 3/28* (2006.01)

(52) U.S. Cl. ........................ 356/326; 356/330; 356/310; 250/223 R; 250/910; 209/577

(58) Field of Classification Search ................. 356/326, 356/330, 310; 250/223 R, 910, 577; 209/577, 209/580, 581
See application file for complete search history.

(56) References Cited

U.S. PATENT DOCUMENTS

| | | | |
|---|---|---|---|
| 4,057,146 A | 11/1977 | Castaneda et al. | |
| 4,093,991 A | 6/1978 | Christie et al. | |
| 5,040,889 A | 8/1991 | Keane | |
| 6,657,722 B1 * | 12/2003 | Nagayoshi ................... | 356/326 |

FOREIGN PATENT DOCUMENTS

| | | |
|---|---|---|
| JP | 176747/1987 | 11/1987 |
| JP | 06-288903 | 10/1994 |
| JP | 06288903 A * | 10/1994 |
| JP | 07-229840 | 8/1995 |
| JP | 08-201273 | 8/1996 |
| JP | 10-15499 | 1/1998 |
| JP | 10202205 | 8/1998 |
| JP | 11051854 | 2/1999 |
| JP | 11091932 | 4/1999 |

OTHER PUBLICATIONS

*English Abstract of JP 10202205.
*English Abstract of JP 11051854.
*English Abstract of JP 11091932.

* cited by examiner

*Primary Examiner*—Layla Lauchman
(74) *Attorney, Agent, or Firm*—Reed Smith LLP

(57) ABSTRACT

An internal qualities inspection system having a receiving tray for placing an inspecting object thereon with a receiving seat and a transmission light passage formed in the receiving tray is arranged to detect light transmitted through the object from below the receiving tray. The inspection system is capable of efficiently detecting the transmission light from inside of each of inspecting objects of varied shapes and varied kinds by adjusting the quantity of light projected on the object according to its size and kind. The system includes in combination a light receiving part and a calibration arrangement which are not affected by any disturbance light to ensure a highly reliable measuring accuracy. In the system, a light projecting part is arranged to project light on the inspecting object from many lamps from both the right and left sides of a transport path; the light receiving part has a light reducing filter arranged between a condenser lens and a spectrometer to adjust the quantity of light incident on the spectrometer; and calibration is made by retractably moving a white level calibrating plate forward to cover the upper surface of each of empty receiving trays when more than a predetermined number of empty receiving trays consecutively travel.

12 Claims, 9 Drawing Sheets

TWO-SIDE MULTIPLE LAMP ONLINE INNER PART INSPECTION APPARATUS

CROSS-REFERENCES TO RELATED APPLICATIONS

This application claims priority of International application No. PCT/JP00/06477 filed Sep. 21, 2000 and Japanese Application No. Hei 11-271151 filed Sep. 24, 1999, the complete disclosures of which are hereby incorporated by reference.

BACKGROUND OF THE INVENTION a) Technological Field

This invention relates to an online internal qualities inspection system for non-destructively inspecting and measuring the internal qualities such as sugar forming degree, acidity, etc. of the objects of inspection, such as agricultural products, by projecting beams of light on each of the objects from on both the right and left sides thereof and by receiving and spectrally analyzing the light transmitted through the objects of inspection while they are in the process of being conveyed on receiving trays or the like by various transport means.

b) Background Art

The types of known methods for measuring the internal qualities of agricultural products include a reflection light type method and a transmission light type method. In the case of the former type, information on the internal qualities is detected through a reflection light obtained from the agricultural product by projecting on the agricultural product beams of light including near infrared rays. In the latter, information on the internal qualities is detected from the transmittance through the agricultural product of the light projected on the agricultural product.

According to the reflection light type method disclosed, for example, in Japanese Laid-Open Patent Application No. HEI 6-300681, the method is carried out by projecting beams of light including near infrared rays onto a measuring (inspecting) object and by detecting the information on the internal qualities of the object from the light reflected by the object as a result of light projection thereon. In carrying out the method, a conventional screening (sorting) device having receiving trays arranged to convey agricultural products one by one is used as it is. However, the internal qualities information obtainable by this method is limited to information on a peripheral part and a part near to it of the agricultural product where the projected light is received. Although this method is applied to a fruit having a thin skin, such as peaches and pears, the internal qualities information obtained by this method fluctuates according to the parts of even one and the same agricultural product. It gives a good result of inspection for a part which has been on a sunny side and a bad result for a part which has been on a shadowy side. It is also incapable of detecting such a honey forming part located deep inside and near to the core of a fruit. Besides, in the event of a fruit having a thick skin, the method gives information only on the thick skin part and not on the edible, flesh part of the fruit.

A system using the transmission light type method was disclosed in Japanese Laid-Open Patent Application No. HEI 7-229840. In this system, a single unit of light projecting lamp is arranged as a light source on one side of the transport path of a transport belt conveyer. A light receiving part is arranged opposite to the light projecting lamp to have an optical axis straightly across the transport path. The system is thus arranged to project light on one side of an agricultural product being conveyed for inspection and to detect light transmitted sidewise through the agricultural product from the other side thereof. However, since the system has only one light projecting lamp, the light projected is limited in intensity and quantity. In the event of an agricultural product having a thick skin or a low water content in its flesh part, therefore, the transmitted light is too weak for spectral analysis. In such a case, therefore, errors in the results of spectral analysis tended to increase to degrade the accuracy of measurement made by the system of this type in the past.

Further, the measured value obtained by the above-stated system by projecting light from one light projecting lamp fluctuates greatly according to the direction in which the light is projected by the lamp to lower the accuracy and reliability of measurement. Another shortcoming of the system lies in that, since the light receiving part is arranged to have a diffraction grating directly connected thereto, the size of a case required for housing the light receiving part therein becomes too large.

The above-stated system is arranged lo shut off the rays of light of the light projecting lamp by means of a shutter solenoid when the light projection is not required in the case of a suspension of operation or the like. However, while rays of projection light is shut off, variations of disturbance light such as ambient light or the like tend to come through a condenser lens into the light receiving part to cause fluctuations in the zero level (dark current) of a light receiving element.

Further, in order to cause light to penetrate a thick-skinned agricultural product, such as oranges, melons, watermelons or the like, with a single light projecting lamp used, the lamp must be arranged to have a high degree of output. However, the use of a high-output lamp necessitates some lamp cooling arrangement as the lamp generates high temperature heat. Besides, since the light is converged onto the agricultural product by means of a reflection mirror, the light converging part is heated to such a high temperature that exceeds 500 degrees. The high temperature has necessitated use of a heat resisting material and presented the hazard of fire. Further, the filament of the high-output lamp is large. The large filament of the lamp not only makes the light converging arrangement difficult but also has a short service life. The lamp thus cannot be used over a long period of time, because its illuminating power gradually decreases.

In view of these problems, the applicant of the present application has developed and practicalized internal qualities inspecting devices of the transmission light type which are capable of detecting information on the internal qualities of citrus fruits or oranges, melons, watermelons, etc. having thick skin parts and the honey forming parts or brown scarred parts existing deep inside of apples or the like. These devices are disclosed in Japanese Laid-Open Patent Applications No. HEI 6-288903 and No. HEI 10-202205. Each of these devices is arranged to use transport means having agricultural product receiving trays. Each of the receiving trays is provided with a receiving seat which is arranged to shield, from disturbance light, a weak light transmitted through the inside of the agricultural product under inspection. The receiving seat is provided with a transmission light passage which vertically penetrates the receiving seat. The light receiving part of the device is arranged to be opposed to the lower center part of each of the receiving trays when they are traveling. Since the transport means is using the receiving trays which are thus arranged for the internal qualities inspecting device, the device can efficiently detect the transmitted light. However, if the device is arranged to be capable of sufficiently obtaining the transmission light from the object of inspection even in the case where the object is of such a kind that does not readily transmit the light, the operational amplifier of a spectral analyzer would come to overflow to make internal qualities analysis impossible.

Further, in order to assure an online internal qualities inspection device stably operates over a long period of time, the device must be constantly calibrated, because of variations taking place in environment temperature in the morning, daytime and evening and variations taking place during the lapse of operation time. However, conventional online internal qualities inspection devices are provided with no mechanism necessary for stably calibrating them.

In addition to this problem, the variations in environment temperature and the lapse of the operation time have caused deviations of a calibration curve.

OBJECT AND SUMMARY OF THE INVENTION

This invention is directed to the elimination and solution of the problems of the prior art mentioned above.

It is therefore an object of this invention to provide an online internal qualities inspection system capable of solving the above-stated problems and applicable to an inspection facility wherein receiving trays are arranged to carry agricultural products one by one; each of the receiving trays has a light-blocking receiving seat formed at an upper part thereof to annularly and elastically engage the agricultural product and a transmission light passage formed to vertically penetrate the receiving tray; and light transmitted through the agricultural product is detected through the light passage. The inspection system according to this invention is arranged to increase the quantity of projection light by projecting beams of light from both the right and left sides across a transport path and to project light over a wide range of surface areas of the agricultural product by using a light projecting part which has a long service life and an illuminating power not decreasing over a long period of time. This arrangement enables the system to be capable of efficiently detecting light transmitted through the object of inspection (agricultural product) to a light receiving part irrespective of the object's light transmissibility which varies according to the size, kind or item of the object. It is another object of this invention to provide an online internal qualities inspection system which is arranged to include means for preventing the operational amplifier from overflowing in the event of a readily light transmissible object; a light receiving part and calibration means which are not readily affected by disturbance light; and means for correcting deviations of a calibration curve due to aging variations or the like. That arrangement enables the invented inspection system to have measuring accuracy with a high degree of reliability.

To attain the above-stated objects, this invention is characterized as described below:

In accordance with the invention, an internal qualities inspection system, wherein the system uses transport means having receiving trays for conveying the objects of inspection thereon one by one; each of the receiving trays has a vertical penetrating transmission light passage formed at its center part and a light-blocking receiving seat arranged at its upper part to annularly, elastically and fittingly engage an object of inspection; light projecting means is arranged to project beams of light on each object of inspection at a predetermined position of the transport means with a plurality of light projecting lamps; transmission light coming through the inside of the object of inspection as a result of light projection by the light projecting means is detected from below the receiving tray through the transmission light passage by light receiving means; and the internal qualities of the object of inspection is inspected by spectrally analyzing the transmission light. The system is arranged according to the invention as follows:

The light projecting means has many light projecting lamps arranged on both the right and left sides in the direction of the width of the object carrying (transport) path of the transport means to concentratedly project beams of light on the right and left sides of the object on each receiving tray, from different light projecting positions and at different angles covering a wide surface area ranging from an obliquely front area to an obliquely rear area on each side of the object, when each receiving tray is at an inspecting position. The light receiving means is provided with a condenser lens for converging, from below the receiving tray, the light transmitted through the transmission light passage. The condenser lens is combined with a spectrometer through a combining mount part, which is provided for leading the condensed transmitted light to the spectrometer.

According to this invention, beams or rays of light are projected by many lamps in a concentrative manner nearly uniformly on a wide surface area of the inspecting object ranging from an obliquely front area to an obliquely rear area on each of the right and left sides of the object with the lamps arranged on both the right and left sides in the direction of the width of the transport path. The system is thus arranged to project light in a large quantity using many lamps over a large area from many different directions and to converge the transmitted light from below the receiving tray through the transmission light passage to obtain through many internal parts of the object a large amount of information on the internal qualities. Therefore, even in cases where the sugar content of the agricultural product which is the inspecting object unevenly exits according to the sunny side and the shadowy side of the object or where denatured scars are variously located, the arrangement reliably gives highly accurate results of inspection.

An internal qualities inspection system according to this invention is arranged as follows: In the above system, the combining mount part of the light receiving means is provided with an incident (light entrance) face of an optical fiber at a focal point position of the condenser lens. The transmitted light which is converged is thus arranged to be led to the spectrometer through the optical fiber.

According to this aspect of the inventive arrangement, transmitted light is arranged to be led from the condenser lens combining mount part of the light receiving means to the spectrometer by means of the optical fiber. Therefore, even in cases where a space available below the receiving tray transport path of a transport conveyer is relatively small or narrow, the spectrometer can be set in a position located away from the light converging part of the light receiving means. The arrangement thus permits use of, in combination with transport conveyers of varied kinds, a spectrometer which is arranged in a large size to have a high spectral performance.

An internal qualities inspection system according to this invention is characterized in that, in the original system described above, the combining mount part of the light receiving means is arranged to adjust the position of an incidence slit of the spectrometer to the focal point of the condenser lens.

According to this aspect of the inventive arrangement, the condenser lens and the spectrometer are combined into one unified body. In this case, therefore, the structural arrangement of the system becomes simpler than that of the system which includes the optical fiber. The simpler structural arrangement has advantages in that an attenuation loss taking place before the transmitted light converged reaches the spectrometer becomes smaller and that assembly work on the system becomes easier. This arrangement is applicable to a case where a relatively large space is available below the receiving-tray transport path of the transport conveyer and the quantity of light transmissible through the inspecting object is small.

An internal qualities inspection system according to another aspect of the invention is defined wherein light reducing filters of varied kinds are arranged to be selectively inserted in between the condenser lens and the spectrometer, so that the quantity of light coming into the spectrometer can be reduced as desired by switching the use of these filters from one over to another.

According to this arrangement, in cases where the transmissible light quantity of the object of inspection varies with the kind of the object, the quantity of light coming into the spectrometer can be adequately adjusted by selectively switching the use of the light reducing filters from one filter over to another. Therefore, the amplification factor of an operational amplifier of the spectral analyzer can be preset at a value suited for the kind of the inspecting object having a small transmissible light quantity. When the item or kind of the object to be inspected is changed over to another kind having a larger transmissible light quantity, such as tomatoes, the operational amplifier can be prevented from overflowing to hinder the spectral analysis with the light coming into the spectrometer reduced by the action of the light reducing filter.

An internal qualities inspection system according to this inspection in accordance with the invention is characterized in that, a light receiving shutter is arranged in a light receiving light passage, between the condenser lens of the combing mount part and the spectrometer, to cut off the passage of the transmitted light and to perform an opening-and-closing shutter action every time one receiving tray passes with the object of inspection placed thereon. The shutter is thus arranged to open when the transmission light passage provided in the receiving tray is in the visual field of the condenser lens and to close when it goes out from the visual field, so that no light is allowed to come into the spectrometer while the inspecting operation is not performed.

According to this arrangement, the light receiving shutter which acts to block the light passage between the condenser lens and the spectrometer opens to allow the transmission light to enter the spectrometer when the transmission light passage which is vertically formed through the center part of each receiving tray comes to an inspecting position right above the condenser lens with the inspecting object placed on the tray. The light receiving shutter does not open when no inspecting object is on the receiving tray, that is, in the event of an empty tray. Further, since the light receiving shutter is arranged to close when the transmission light passage of the receiving tray comes to a position deviating from the inspecting position in front of the condenser lens, no light other than the transmission light is allowed to enter the spectrometer. The arrangement thus ensures a stable operation without any adverse effect of increase in temperature taking place inside of the spectrometer or at an amplification circuit, etc.

An internal qualities inspection system according to this invention is also defined wherein the condenser lens of the light receiving means is disposed at a position close to the transmission light passage which is formed to vertically penetrate each of the receiving trays; a dust-proof lens hood is arranged to secure a visual field on the object side with a light receiving window of transparent glass formed in front of the lens hood; and dust-proof means is arranged to blow air at the outer side of the transparent glass from the peripheral part toward the middle part of the window.

According to this arrangement, dust existing within the visual field of the condenser lens of the light receiving means can be blown away even though the condenser lens is arranged in an upward facing posture below the transmission light passage of the receiving tray. Therefore, the condenser lens can be arranged below the receiving tray to adequately receive the transmitted light in the upward posture.

An internal qualities inspection system according to this aspect of the invention is characterized in that the system is defined as follows: The system is provided with a mechanism for moving back and forth a white level calibrating plate. The white-level-calibrating plate moving mechanism is arranged to move forward the white level calibrating plate from outside of the receiving tray transport path in such a way as to cover the receiving seat of the tray with the white level calibrating plate when no inspecting object is on the receiving tray at the inspecting position where the light projecting means and the light receiving means are arranged. When a predetermined number of such empty receiving trays consecutively pass the inspecting position, calibration can be automatically carried out by covering the receiving seat of each of the receiving tray with the white level calibrating plate.

This arrangement has the following advantage: The overall output value of the system comes to fluctuate due to variations of environment temperature or deterioration of lamps and an optical system taking place according as operation along with the time lapse of the operation. For spectral analysis, a calibrating action is performed to correct the output value fluctuations before a start of operation, during a break or after a temporary suspension of operation. In addition to that, the calibrating action can be automatically carried out, by moving the white level calibrating plate back and forth, even while the system is in operation, when a plurality of empty receiving trays (without having any agricultural product thereon) consecutively come to pass the inspecting position.

An internal qualities inspection system according to another aspect of this invention is characterized in that, in the system defined, the light projecting means which has many light projecting lamps is arranged to be provided with means for increasing or decreasing a number of light projecting lamps to be lighted up according to the light transmissible degree of the inspecting object which varies with the size or kind of the object.

According to this arrangement, the number of light projecting lamps to be lighted up is changed according to the light transmissible degree (difficulty or easiness of light transmission) of the inspecting object. This arrangement enables the system to effectively carry out the internal qualities inspecting operation over a wide range of objects including thick-skinned agricultural products which do not readily allows light to be transmitted through them, such as water melons, melons; citrus fruits having skins of a medium thickness; and thin-skinned products which readily permit light transmission through them, such as tomatoes, pears, apples and peaches.

An internal qualities inspection system according to another aspect of the invention is characterized in that a light blocking device is arranged in front of the many light projecting lamps of the light projecting means to block beams of light projected on the object of inspection.

With the light blocking device arranged in this manner, when the receiving tray is allowed to be at rest in inspecting the system or during a break of operation, the tray can be protected from the heat of the concentrative projection of light of halogen lamps without putting out the lamps which are alight. More specifically, the light blocking device is arranged to block the beams of light projected on the receiving tray at rest by moving back and forth a light blocking shutter between each of the right and left sides of the receiving tray being conveyed by the transport conveyer and the light projecting means arranged on each of the right and left sides of the receiving tray. The light blocking device effectively prevents the receiving tray from being deformed, denatured or overheated by the heat of the light projected.

Further, the temperature and heat-generating and light-emitting states of the lamps vary every time the lamps are put out and lighted again. Then, the intensity of building-up beams of light and the quantity of light fluctuate to bring about an adverse effect on the accuracy of inspection. To avoid this, the light projecting lamps are left alight by actuating the light blocking device in case where the operation of the conveyer is brought to a stop for a short period of time or in like cases. In such a case, therefore, the beams of light projected can be kept stabilized to enable the system to operate again maintaining its inspection accuracy at the same degree of accuracy obtained before a pause or suspension of operation.

DESCRIPTION OF THE PREFERRED EMBODIMENTS

Figure 1:
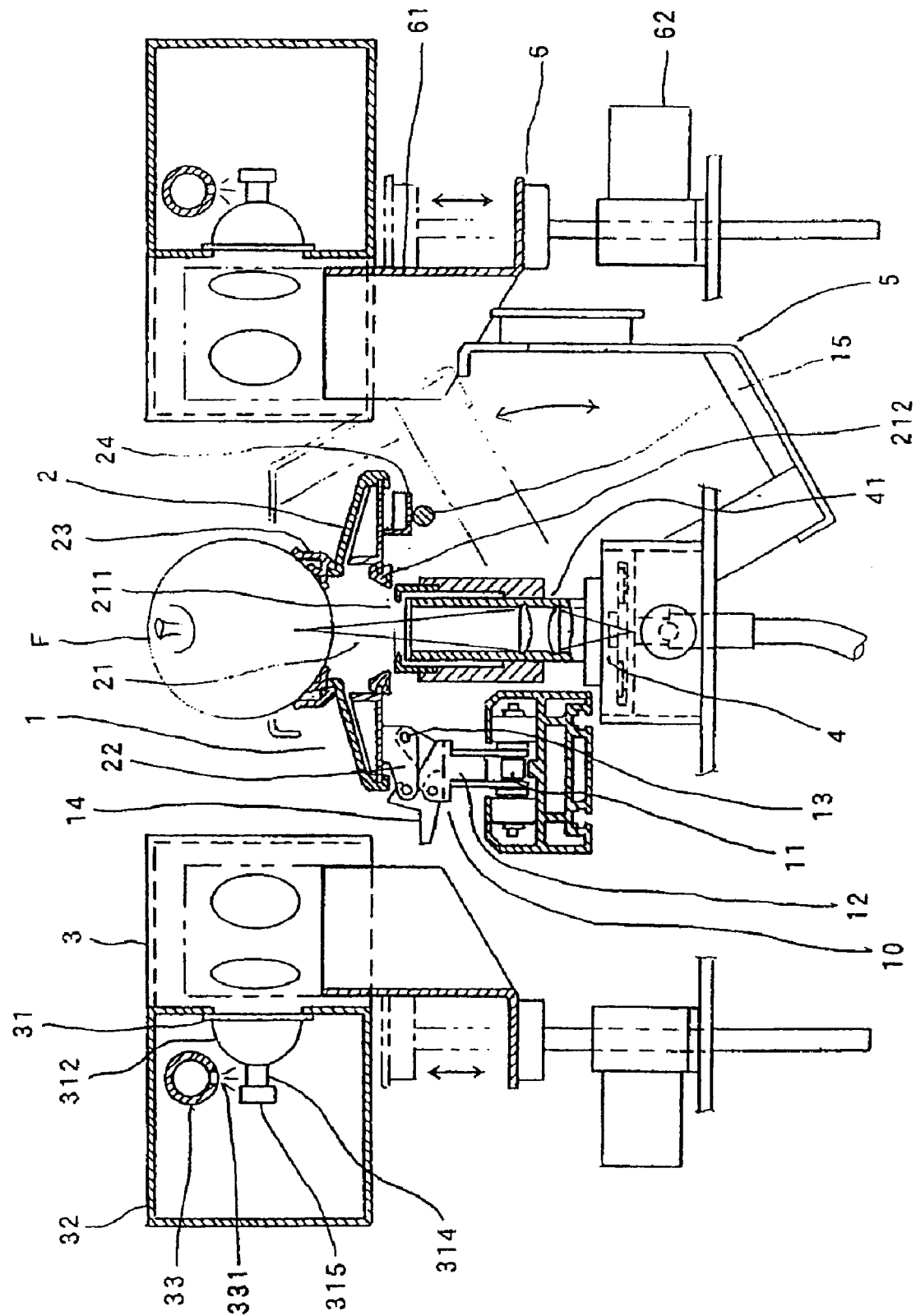
FIG. 1 is a vertical sectional view showing in outline an internal qualities inspection system arranged as a first embodiment of this invention, including light projecting means which is arranged on right and left sides of a receiving tray in a transport path and light receiving means which is arranged below the light projecting means.

A two-side multiple lamp online internal qualities inspection system according to this invention includes receiving trays each of which is arranged to carry thereon an object of inspection and is provided with a light blocking seat having a transmission light passage formed in the middle part of the seat to vertically penetrate the receiving tray.

In the system, the light projecting means has many light projecting lamps arranged across the transport path of a transport conveyer on both the right and left sides in the direction of its width. These light projecting lamps are thus arranged to project beams of light on the object of inspection respectively from different positions and at different angles to cover a wide area of the object ranging from an obliquely front part to an obliquely rear part on each of the right and left sides of the object.

The light receiving means has the condenser lens in an upward posture at a position corresponding to the exit of the transmission light passage in the lower face of the receiving tray. The condenser lens is arranged to converge the light transmitted by the object through the transmission light passage and is provided with a light receiving optical path which is formed to lead the converged light to a spectrometer. The spectrometer is combined with the condenser lens through a combining mount part.

The spectrometer which is in combination with the condenser lens is arranged either in one unit with the condenser lens or disposed away from the condenser lens to be combined with the latter through an optical fiber connected to the combining mount part according to the structural arrangement of the transport conveyer.

In the case where the spectrometer is disposed away from the condenser lens, the light entrance plane of the optical fiber which leads to the spectrometer is disposed in a position of the combining mount part where the focal point of the condenser lens is obtained. Then transmitted light converged by the condenser is led to the spectrometer through the optical fiber. In this case, the spectral analyzing performance of the system can be enhanced by using a large spectrometer.

If the system is arranged to combine the spectrometer and the condenser lens in one unit, the position of an entrance slit of the spectrometer is adjusted to a position of the combining mount part where the focal point of the condenser lens is obtained.

The light receiving optical path is provided between the condenser lens and the light entrance plane of the optical fiber or the entrance slit of the spectrometer.

Means for selectively inserting light reducing filters is arranged at the combining mount part to selectively insert light reducing filters of varied kinds into the optical path. The system thus can be operated to reduce as desired the quantity of light coming into the optical fiber or the entrance slit of the spectrometer.

A light reducing filter mounting plate is provided at the combining mount part which has a sealed outside extending between a light receiving window of the condenser lens and the entrance face of the optical fiber arranged to lead the converged transmitted light to the spectrometer. A plurality of filters having different light reducing rates are mounted on the light reducing filter mounting plate, which is arranged to be operable from outside to selectively use these filters. The light reducing filters are preferably arranged immediately in front of the light entrance plane of the optical fiber where the transmitted light is narrowly converged by the condenser lens toward its focal point.

When the object of inspection is not in a position to be inspected, that is, when the object is before or after the inspecting position, the light receiving window of the condenser lens is blocked from light in a state corresponding to a lower light blocking face formed outside of the exit of the transmission light passage of the receiving tray. The transmitted light is arranged to be converged only when the exit of the transmission light passage comes to the inspecting position. The spectrometer is thus arranged to detect no light when the object is before or after the inspecting position. The arrangement effectively eliminates the possibility of the adverse effect of any light other than the light to be subjected to the spectral analysis.

In the case where no light blocking face can be formed below the transmission light passage on the outside thereof, because of insufficiency of the area of the lower part of the receiving tray or the like, the light receiving shutter is arranged at a position near to the light reducing filter of the combining mount part to allow the transmitted light to pass by opening the light receiving shutter only when the exit part of the transmission light passage comes to the inspecting position. When the exit of the transmission light passage deviates from the inspecting position, the light receiving shutter is closed to allow no transmitted light to come into the spectrometer.

The zero level (dark current) of the light receiving circuit of the spectrometer is detected when the light receiving window of the condenser lens is shield from light by the lower light blocking face of the receiving tray or when the light receiving shutter is closed to allow no light come into the spectrometer.

In online inspecting the inspecting objects F at a high speed, there remains at the light receiving circuit of the spectrometer a residual current of a last inspection process every time the inspection is performed. Then, a next light receiving output is affected by the accumulation of the residual current. To eliminate this adverse effect, spectral analysis is made for the inspection by using the zero level detecting value.

The condenser lens is disposed near to the exit of the transmission light passage provided in the lower face of the receiving tray. A lens hood is arranged on the objective side of the condenser lens to secure a visual field. A light receiving window is formed with transparent glass in front of the lens hood to make a dustproof structure of the lens hood. Dust-proof means is arranged to blow air at the outer surface of the transparent glass from its peripheral part toward its center. The air blowing arrangement ensures that the upper surface of the light receiving window is never soiled with dust or the like.

With the transmitted light coming out from the lower surface of the inspecting object on the receiving tray, the condenser lens receives it from the transmission light passage of the receiving tray through the receiving light window and causes it to converge and focus on the entrance face of the optical fiber which leads to the spectrometer. With the light beams projected in a concentrative manner from different directions on both the right and left sides of the inspecting object, the transmission light coming through the inside of the object to its lower surface thus can be efficiently caused to converge.

The white level calibrating plate moving mechanism is arranged to retractably move the white level calibrating plate forward, from outside of the transport path of the receiving tray, in such a way as to cover the receiving seat of the receiving tray. In cases where the environment temperature is changed at the time of start of operation of the system, or after a temporary suspension of it for a break, or where more than a predetermined number of empty receiving trays consecutively pass, calibration can be made for a stable operation of the system over a long period of time by moving the white level calibrating plate to cover the upper surface of the receiving seat.

The white level calibrating plate is arranged to be retracted from the transport path to its standby position when a sensor disposed at a part of the transport conveyer before the inspecting position detects arrival of the receiving tray at this part with the inspecting object carried thereon.

The large number of light projecting lamps are respectively provided with parabolic reflection mirrors to form such beam angles that cause the projected light focused on the center of the inspecting object and have their front surfaces sealed. With the sealed lamps used, the beams of light of them are caused to converge toward the inspecting object to ensure highly efficient light projection. The high light-projecting efficiency permits use of small lamps. The sealed fronts of the lamps effectively prevent the reflection mirrors from being soiled with dust and from becoming frosty, so that their reflection performance can be prevented from decreasing.

In order that the light is projected on the inspecting object at the inspecting position of the transport conveyer in equal quantities of light covering a wide range of its surface area from obliquely front part to an obliquely rear part on each of right and left sides of it with respect to its traveling direction, these lamps are preferably arranged at equal distance from the inspecting position. An air blowing nozzle is arranged to blow air at the sealed part of each lamp. Heat generated at each lamp body can be dissipated by the air blowing arrangement to prevent overheating, so that the service lives of the light projecting lamps can be increased.

These lamps are lighted up under the control of a control circuit. The control circuit is arranged to permit switching the number of lamps to be lighted up, for example, from all of them to 80% of them, to 60% of them, etc. The number of the lamps to be lighted up is thus adjusted according to the light transmissible degree of the inspecting object to decrease it when the transmission light is strong and to light up all the lamps when the transmissible light is weak. This arrangement makes the system usable for inspecting the internal qualities of inspecting objects of varied kinds.

For the internal qualities inspection system, stability of intensity and quantity of the beams of light projected by the lamps are very important. The accuracy of inspection is affected by the fluctuations of them. Therefore, a sufficient length of preheating time is necessary for building up of the intensity and quantity of the light projected to a stabilized level after the light projecting lamps are lighted up. In view of this, the lamps are preferably not put out when the conveyer is only temporarily stopped for a break of operation or inspection.

When the conveyer is brought to a stop in such a case, the concentrated projection of light tends to overheat the receiving tray to deform or denature the tray. To prevent such overheating, therefore, a light blocking device is arranged to shut off the beams of light projected in such a case.

To shut off the concentrating light projection from many light projecting lamps, the light blocking device is arranged to retractably move a light blocking shutter forward between each of the right and left sides of the receiving tray transport path and the many light projecting lamps.

The light blocking shutter is arranged either to be vertically moveable up and down or to be moveable in parallel with the side parts of the receiving tray with respect to the traveling direction of the tray.

EMBODIMENT 1

This invention is described in detail below through a first embodiment thereof which is a two-side multiple lamp online internal qualities inspection system arranged as shown in FIGS. 1 to 6.

Figure 2:
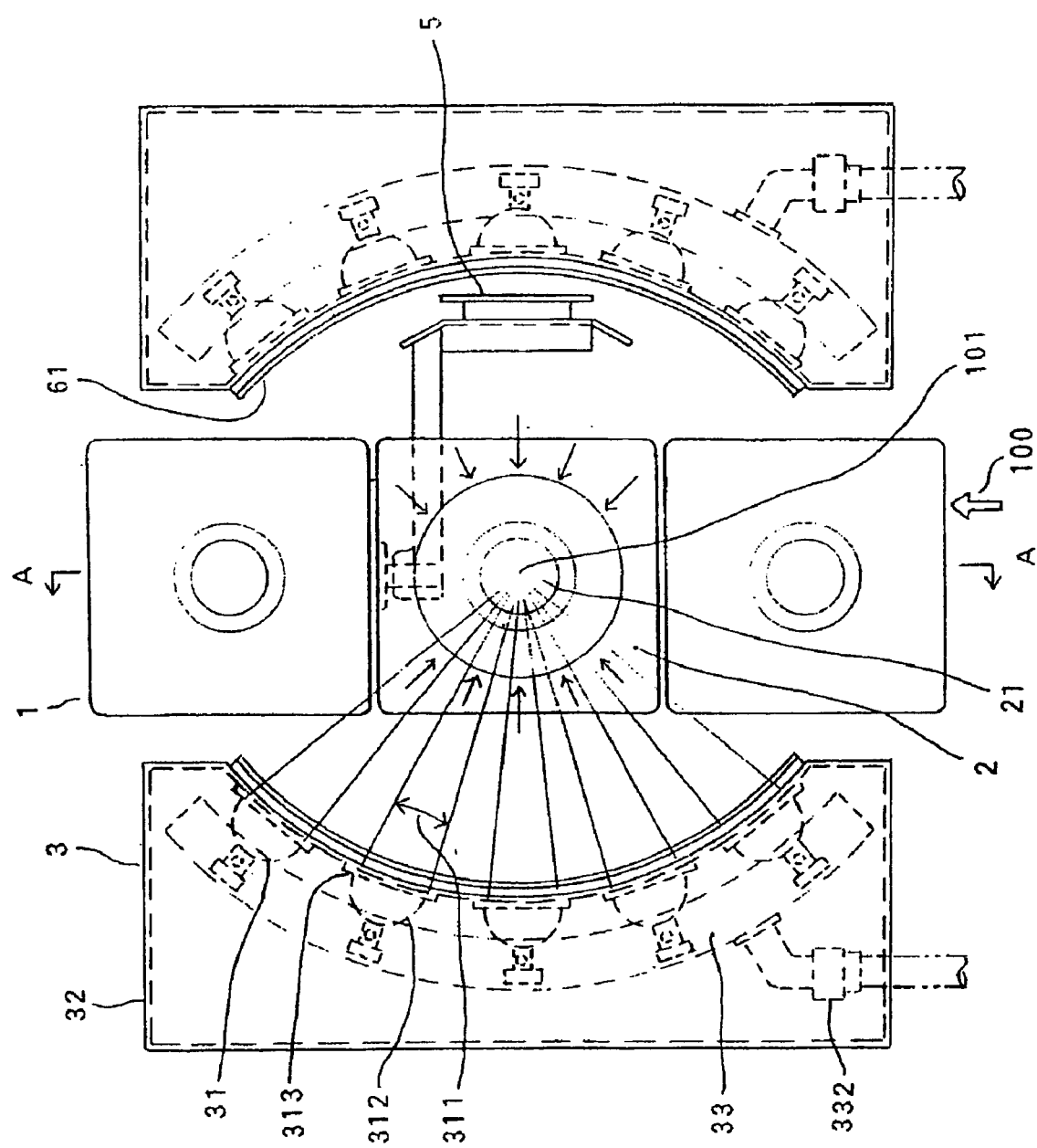
FIG. 2 is a plan view showing the essential parts of the first embodiment.
Figure 3:
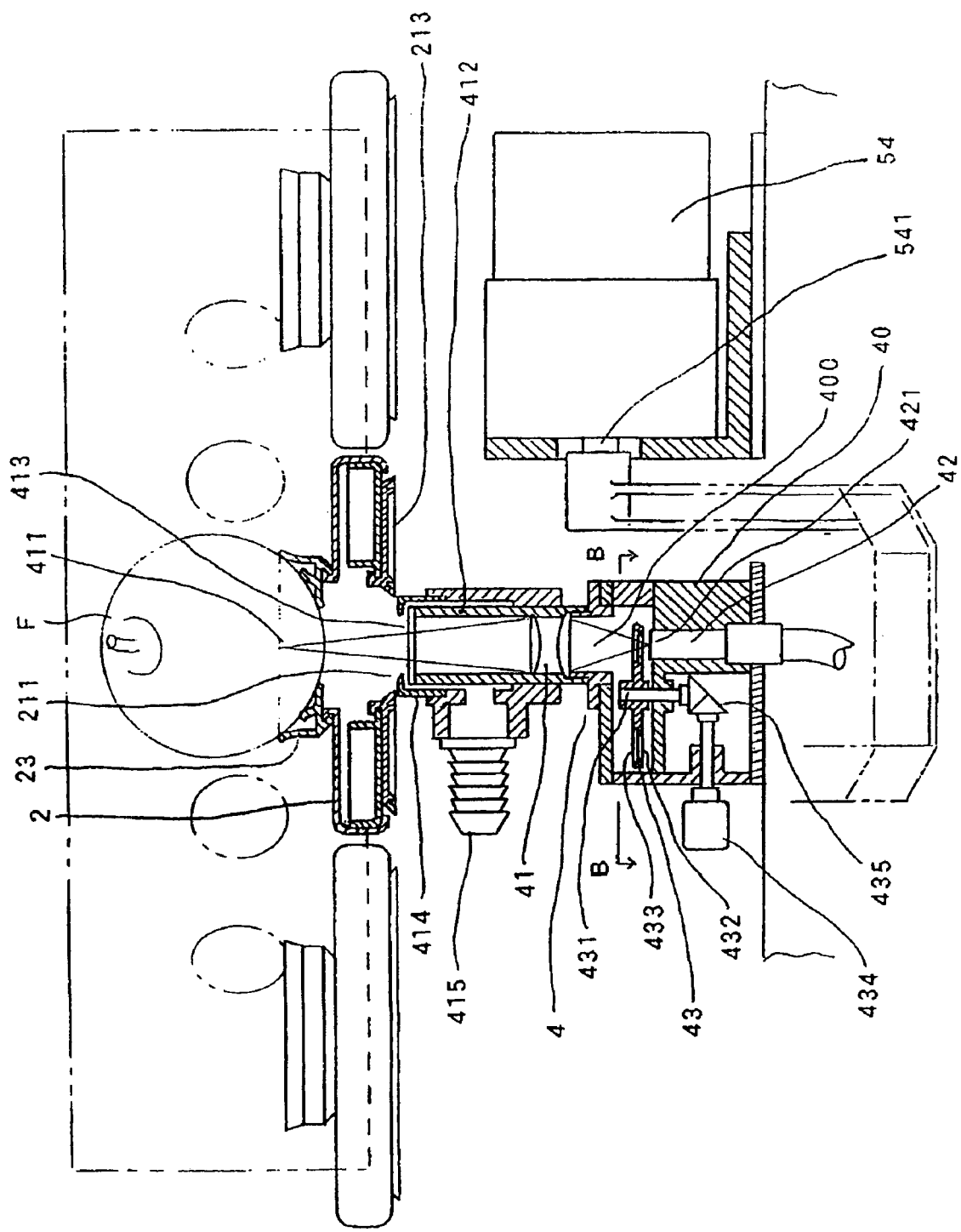
FIG. 3 is a side view of a vertical section taken along a line A—A shown in FIG. 2.

FIGS. 1, 2 and 3 schematically show the essential parts of the system which is adapted for inspecting agricultural products. Referring to these drawings, a transport conveyer 1 is arranged as transport means for conveying one by one the agricultural products F which are objects of inspection on receiving trays 2. Light projecting means 3 is arranged to project beams of light, from both the right and left sides of the transport conveyer 1, on each of the agricultural products F placed on the receiving tray 2. Light receiving means 4 is arranged to receive transmission light transmitted through the inside of each of the agricultural products F.

The transport conveyer 1 (transport means) is arranged to convey in a row the agricultural products F with each agricultural product F placed on each receiving tray 2 one by one. The transport conveyer 1 as shown in FIG. 1 uses a chain conveyer 10 which is provided with the receiving trays 2. The transport conveyer 1, however, does not have to be the one shown in FIG. 1. The chain conveyer 10 may be replaced with any other known conveyer, such as a belt conveyer (shown in FIG. 6) popularly employed in inspecting the appearance of the inspecting objects for their colors, scars and the like, or some other chain conveyer, so long as it is arranged in combination with receiving trays each of which is provided with a vertical through hole as a transmission light passage 21.

Because inspection for internal qualities is often expected to be performed together with inspection for other purposes such as measuring grades in size, appearance, etc. The inspection system embodying this invention is, therefore, arranged to be applicable to transport conveyers adapted to measurement for various purposes in common.

Referring to FIGS. 1 and 2, the agricultural product F is conveyed by the transport conveyer 1 in a state of being put on the receiving tray 2. An inspecting position 101 is set in a transport path where the light projecting means 3 and the light receiving means 3 are arranged in combination. When the agricultural product F comes to pass the inspecting position 101 of the transport path 100, the light projecting means 3 projects beams of light on the peripheral surfaces of the right and left sides of the agricultural product F in various directions with the beams of light blocked by nothing on both sides. The light projected is transmitted to the light receiving means 4 through a transmission light passage 21 with the transmission light blocked also by nothing. The agricultural product P is then carried away to be relieved from the light projection.

Figure 6:
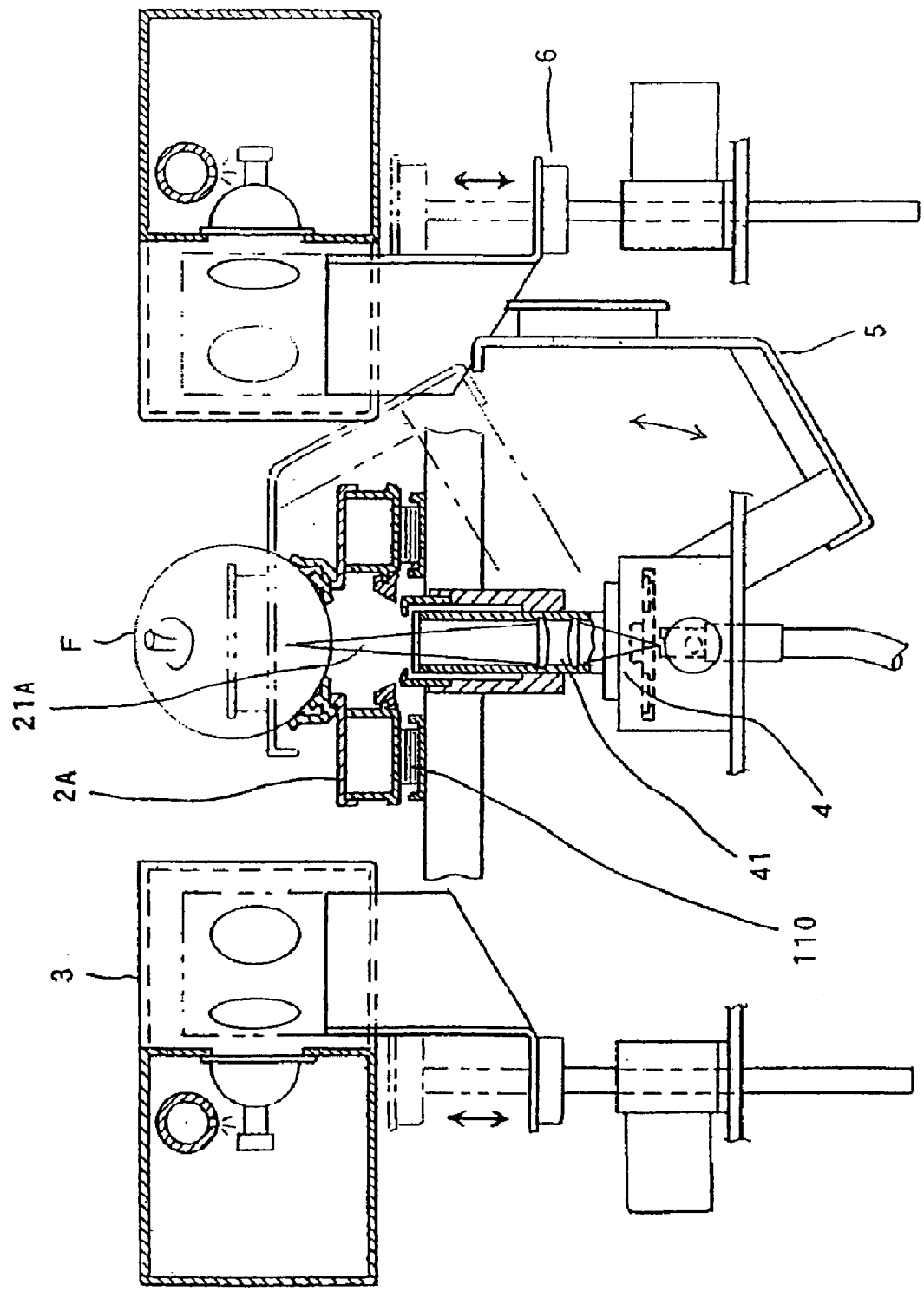
FIG. 6 is a sectional view showing by way of example a case where a belt conveyer is employed as a transport conveyer.

FIG. 6 shows a case where the transport conveyer is a belt conveyer instead of a chain conveyer. In this case, a receiving tray 2A is not connected to the conveyer. In order to assure that nothing hinders the passing of light between a transmission light passage 21A of the receiving tray 2A where the tray 2A is not connected to the conveyer and a condenser lens 41 of the light receiving means 4, the transport conveyer belt 110 is arranged to have a void space in the middle part thereof while it is traveling.

Figure 5:
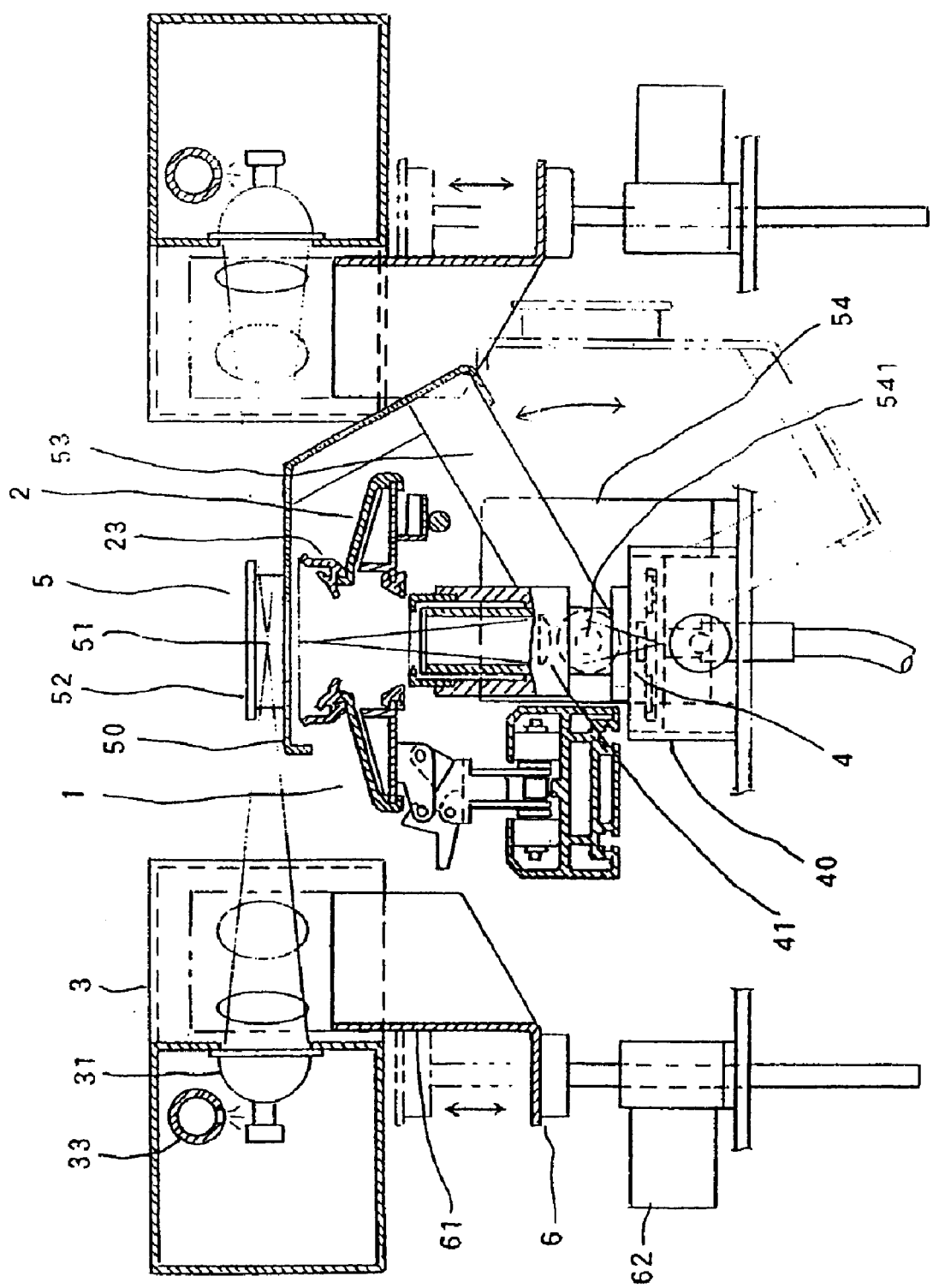
FIG. 5 shows a white level calibrating mechanism which is arranged at the same part as in FIG. 1.

Referring to FIGS. 1 and 5, the conveyer chain 11 of the conveyer 10 is provided with a bracket 12. The receiving tray 2 is mounted on the bracket 12 and arranged to be tiltable sidewise on a fulcrum pin 13 in such a manner that the upper surface of a receiving seat 23 can be kept horizontal by an engaging piece 14.

A sliding part 24 is disposed opposite to a fulcrum part 22 across the transmission light passage 21. The sliding part 24 is supported by a receiving-tray attitude guide rail 15 in such a way as to adjust the exit 211 of the transmission light passage 21 provided in the lower face of the receiving tray 2 to a predetermined level.

The transmission light passage 21 is provided with an exit packing 212. To prevent disturbance light from entering a space between the receiving tray 2 and the light receiving means 4 disposed at the inspecting position, the light passage exit packing 212 is arranged to allow the receiving tray 2 to travel as close to the light receiving means 4 as possible. For this purpose, the transmission-light-passage exit packing 212 has its lower light blocking face 213 formed to extend forward and backward in the direction of travel.

The lower light blocking face 213 is thus arranged to act to shield a light receiving window 413 of the condenser lens 41 from disturbance light in front and in rear of the transmission light passage 21 which is formed in the middle part of the receiving tray 2.

When the light receiving window 413 of the condenser lens 41 of the light receiving means 4 is thus shielded from light by the lower light blocking face 213, the zero level, i.e. a dark current, of a light receiving circuit of a spectrometer which is not shown is detected.

The light projecting means 3 includes a large number of halogen lamps 31. The halogen lamps 31 are mounted within lamp boxes 32. In the lamp boxes 32, the halogen lamps 31 are arranged on both the right and left sides of the transport path 100 of the transport conveyer 1 in the direction of width thereof to concentratedly project beams of light on the agricultural product F on the receiving tray 2 at the inspecting position of the transport path respectively from different positions and at different angles covering a wide area of the product F ranging from its obliquely front part to an obliquely rear part on each of its right and left sides. The beams of light is thus arranged to be projected toward the center of the agricultural product F.

Each of these halogen lamps is of a relatively small size and is provided with a parabolic reflection mirror 312 for forming a beam angle which gives a focal point at the inspecting position. The front side of each halogen lamp is preferably sealed with a seal 313 which is made of heat resisting glass.

Small lamps can be lighted up at a low voltage and permit reduction in size of filament. The use of small lamps, therefore, enhances light converging efficiency. Besides, their Nichrome wire diameter is relatively thick to give a long service life.

As shown in FIGS. 1 and 2, the large number of halogen lamps 31 are preferably arranged in a sectoral alignment on both the right and left sides of the transport path at equal distances from the inspecting position. The alignment of the halogen lamps 31 may be vertically arranged in a plurality of steps. Each of the halogen lamps 31 is set in a position of having its focal point on the optical axis at the center of the agricultural product F when the agricultural product F is at the inspecting position 101.

An air blowing duct 33 is arranged along a sealing part 314 and at the position of a socket 315 of each of the halogen lamps to blow air at the sealing part 314 of the lamp 314 from an air blower through an air blowing nozzle 331. The air blowing arrangement prevents overheat by dissipating heat generated at the sealing part 314, the socket 315 and the lamp body.

The air is supplied by connecting the air blower which is not shown to a connection port 332 through a suitable air blowing means.

The halogen lamps 31 is arranged in a large number to be capable of projecting a quantity of light necessary for obtaining sufficient transmission light even from such an agricultural product that does not readily transmit light. However, in cases where the object of inspection is an agricultural product readily transmitting light, such as a tomato or the like, the number of lamps to be lighted up is reduced. For this purpose, an electric circuit is arranged to include means for selectively increasing and decreasing the number of lamps to be lighted up according to the object to be inspected.

The light receiving means mainly consists of, as shown in FIG. 3, the condenser lens 41; an optical fiber 42 which leads transmission light converged by the condenser lens 41 to a spectrometer which is not shown; and a light-reducing-plate mounting plate 43 which is disposed in front of the light entrance plane 421 of the optical fiber 42. A mounting part 40 is arranged to have these main parts mounted in combination thereon and to form a dark room.

The condenser lens 41 is arranged to have an object-side focal point 411 at a transmission light entrance formed at the center of the upper face of a receiving seat 23 which is arranged to have the lower side of the inspecting object F on the receiving tray 2 there when the tray 2 is at the inspecting position 101. The condenser lens 41 is provided with a cylindrical lens hood 412 which extends to a position near to the exit 211 of the transmission light passage 211 located on the lower side of the receiving tray 2; and a light receiving window 413 which is made of transparent glass and is located in front of the condenser lens 41.

A dust-proof hood 414 is arranged to have air blown from the peripheral part of the lens hood 412 toward the center of the outer surface of the light receiving window 413. The dust-proof hood 414 is mounted to have its upper end face as close as possible to the exit 211 of the transmission light passage of the receiving tray 2. The air is arranged to be supplied from an air blower which is not shown but is connected to a connection port 415 through suitable means.

With the lens hood 412 arranged in an upward facing state below the receiving tray 2 which is being conveyed, air is blown at the upper surface of the light receiving window 413 to prevent dust or some foreign matter from hindering a visual field. Meanwhile, the lens hood 412 blocks disturbance light from coming from around the condenser lens 41. By virtue of this arrangement, only the transmission light coming from the front of the visual field defined by the light receiving window is efficiently allowed to come into the condenser lens 41.

The optical fiber 42 is set by adjusting its light entrance plane 421 to the focal point of the condenser lens 41. The transmitted light coming from the light receiving window 413 of the condenser lens 41 is converged on the light entrance plane 421 and led to the spectrometer through this optical fiber 42. Upon receipt of the transmission light, the spectrometer performs spectral analysis.

Figure 4:
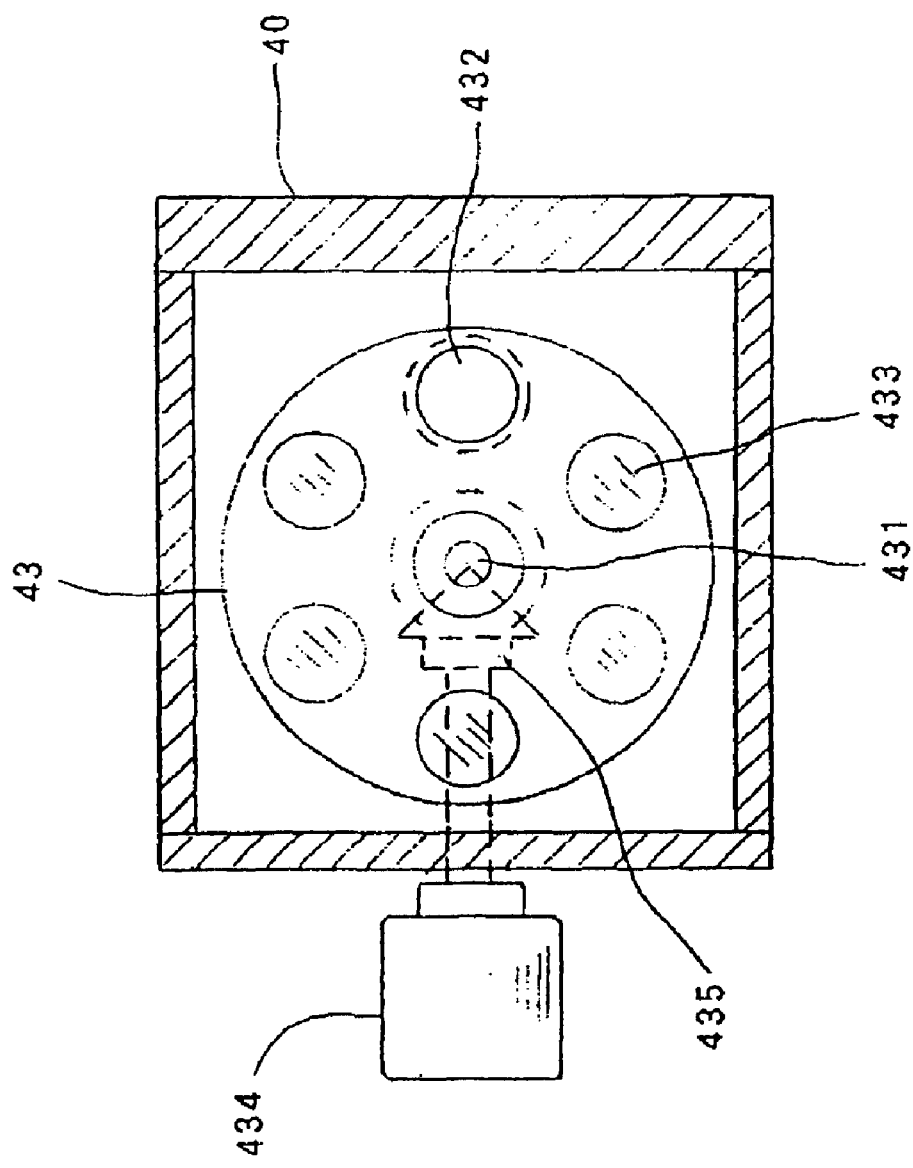
FIG. 4 is a plan view of a section taken along a line B—B shown in FIG. 3.

As shown in FIGS. 3 and 4, a light-reducing-filter mounting plate 43 which is in a disk-like shape is mounted on a shaft 431 disposed on one side of an optical fiber mounting part. The disk-like shape of the filter mounting plate 43 is large enough for completely blocking a light receiving optical path 400 provided for the transmitted light which is converged on the light entrance plane 421 of the optical fiber 42.

The filter mounting plate 43 is provided with filter mounting holes 432 which are circularly arranged around the shaft 431 at a plurality of evenly spaced positions to have a radius from the shaft 431 and an optical axis where the transmitted light is converging. Among these filter mounting holes 432, one of them is left blank while light reducing filters 433 of different light reducing rates are mounted on all other holes.

In other words, the light-reducing-filter mounting plate 43 is mounted on the shaft 431 with the position of each of the filter mounting holes 432 adjusted to the center of the light receiving optical path 400 which is provided for allowing the received transmitted light to pass between the condenser lens 41 and the light entrance plane 421 of the optical fiber 42.

For the selective use of one of the light reducing filters 433 of the light-reducing-filter mounting plate 43, a knob handle 434 disposed outside of the system is operated to rotate the shaft 431 which is mounted through a miter gear 435.

The light-reducing-filter mounting plate 43 is disposed within a combining mount part 40 which forms a dark room by encompassing a part of the embodiment extending from the condenser lens 41 to the light entrance plane of the optical fiber 42 to prevent an adverse influence of disturbance light.

The embodiment is provided with a white level calibrating means 5. FIG. 5 shows the white level calibrating means 5 as in process of a calibrating action. A white level calibrating plate 51 is mounted on the mounting part 50 of a retaining metal 52.

A mounting arm 53 is mounted on the output shaft 541 of a stepping motor 54 which is disposed adjacent to the combining mount part 40 of the light receiving means 4. In performing a calibrating operation, the mounting arm 53 is operated by rotating the stepping motor 54 forward or backward to move the white level calibrating plate 51 to the front of the condenser lens 41 above the receiving seat 23 of the receiving tray 2 or to retract it from the transport path of the transport conveyer 1.

The mounting part 50 of the white level calibrating plate 53 is formed to be capable of covering an area wider than the upper surface of the receiving seat 23 and has surrounding parts arranged to block the projected light of the lamps on both sides from coming directly into a part between the white level calibrating plate 53 and the upper surface of the receiving seat 23.

The retaining metal 52 is arranged to have an open peripheral part to allow the white level calibrating plate 51 to be illuminated with the light of the plurality of halogen lamps on both the right and left sides of the transport path with respect to the direction of width thereof. The light transmitted through the white level calibrating plate 51 passes through the receiving seat 23 and reaches the spectrometer after it is converged by the condenser lens 41.

The mounting arm 53 is formed in a bent shape to prevent it from interfering with the receiving tray transport path and the light receiving means 4. When the calibrating action is not required, the mounting arm 53 is swung to retract the white level calibrating plate 51 downward from one side of the transport path. When calibration is necessary at a start of the internal qualities inspection system or in the event of variations in environment temperature after a temporary suspense of the inspecting operation for a break, or the like, the calibration is carried out by causing the mounting part 50 to cover the receiving seat 23 from above when a predetermined number of empty receiving trays consecutively pass the inspecting position. By virtue of the arrangement to perform the calibration in this manner, the inspection system can be stably used over a long period of time.

The white level calibrating plate 51 is retracted outside of the transport path when a sensor provided for a process before the inspecting position 101 of the transport conveyer 1 detects that an agricultural product is on the receiving tray 2.

A light blocking device 6 is arranged to shut off the beams of light projected. The light blocking device 6 consists of a light blocking shutter which shuts off the projection light to protect the receiving tray 2 from the heat of concentrating projection light in cases where the receiving tray 2 is brought to a stop for a check or the like; and a motor 62 which is arranged to vertically move the light blocking shutter upward or downward. The motor 62 is preferably of a linear motion driving type having a rack-and-pinion mechanism incorporated therein.

As shown in FIG. 2, the light blocking shutter 61 is formed along the front shape of each of the lamp boxes 32 to block the light projected from each lamp. In doing online inspection in a normal manner with the transport conveyer on the run, the light blocking shutter is moved downward away from the front of the lamp box to allow light projection.

For the internal qualities inspection system, the intensity of light projected by the lamps and the stability of quantity of the light are very important. If the lamps are put out and lighted up again when the conveyer is brought to a stop for a check or a break of operation only for scores of minutes, for example, the intensity and quantity of the light projection vary and become unstable, because the temperature, heat generation and light emitting state of the lamps vary every time they are put out and lighted up again.

Therefore, when the transport conveyer is stopped for a relatively short period of time like in the above-stated case, the stableness of light projection is maintained by leaving the lamps alight with the light blocking device actuated to protect from the heat of light projection the receiving trays, etc. which are otherwise under the concentrating light projection.

A calibration curve can be prevented from deviating by this arrangement.

EMBODIMENT 2

A second embodiment of this invention is an internal qualities inspection system arranged as shown in FIGS. 7 to 10.

In the second embodiment, a combining mount part 40B is arranged to connect a condenser lens 41B directly to a spectrometer 7B. The position of an incidence slit 71B of the spectrometer 7B is adjusted to the focal point of the condenser lens 41B in combining the spectrometer with the condenser lens 41B. A light receiving shutter 44B is arranged to shut off the passage of transmission light between the condenser lens 41B and the spectrometer 7B.

A light blocking device 6B for blocking the projection light of light projecting means 3B is arranged differently from the light blocking device 6 of the first embodiment.

Figure 7:
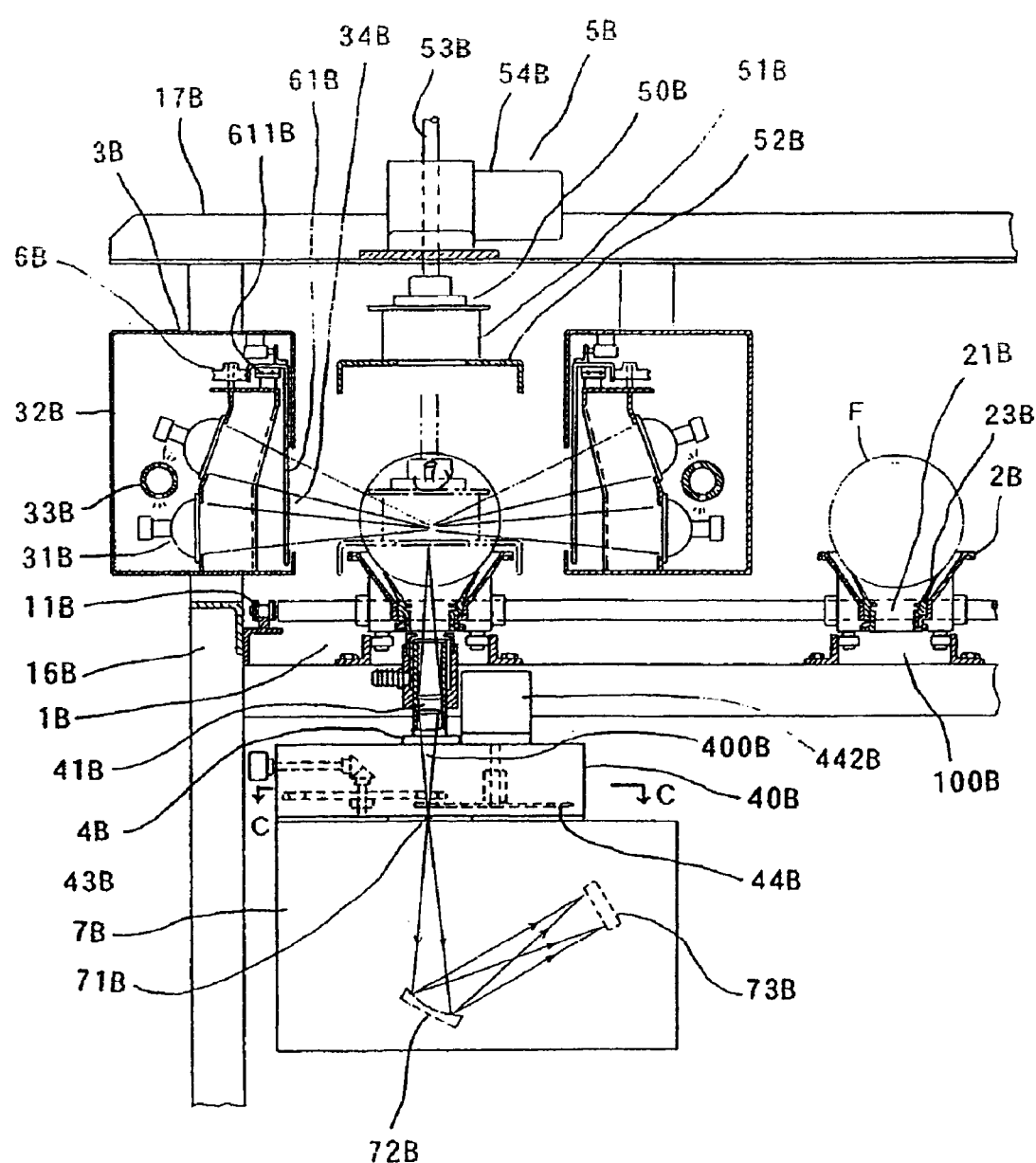
FIG. 7 is a vertical sectional view showing a second embodiment of this invention wherein a chain conveyer having receiving trays arranged thereon in a plurality of strips of transport paths is employed and light projecting means is arranged on right and left sides of each of the strips across the receiving trays while light receiving means is arranged below the light projecting means.

FIG. 7 shows the internal qualities inspection system as applied to a transport conveyer 1B which is adapted for processing agricultural products F in a large quantity.

In the transport conveyer 1B, chain rails are arranged respectively on the two inner sides of a conveyer frame 16B. Chains 11B are endlessly stretched on the chain rails. Receiving tray mounting members are arranged in parallel with each other and are mounted on the chains 11B at their right and left ends on both sides of the conveyer.

A plurality of receiving trays 2B are mounted in a row on each of the receiving tray mounting member 18B. A plurality of transport paths are formed by spacing each receiving tray 2B from another to have a sufficient space for installing light projecting means 3B there. In other words, the light projecting means 3B is installed in between the strips (columns) of the receiving trays 2B.

Each of the receiving trays 2B is arranged in the same manner as in the case of the first embodiment to have a transmission light passage 21B vertically penetrate the center of it and to convey an inspecting object F with the object F placed on a receiving seat 23B of the receiving tray 2B.

The light projecting means 3B and light receiving means 4B are arranged at each of inspecting positions arranged at each strip (transport path) of the receiving trays 2B. The inspecting positions of the strips are arranged to deviate from each other in a zigzag manner in the traveling direction of the conveyer 1B. The conveyer 1B is arranged to have the strips of the receiving trays 2B not excessively spaced from one another.

Halogen lamps 31B to be used for projecting light and air blowing ducts 33B are arranged in the same manner as in the case of the first embodiment. Therefore, the details of them are omitted from the following description.

Figure 8:
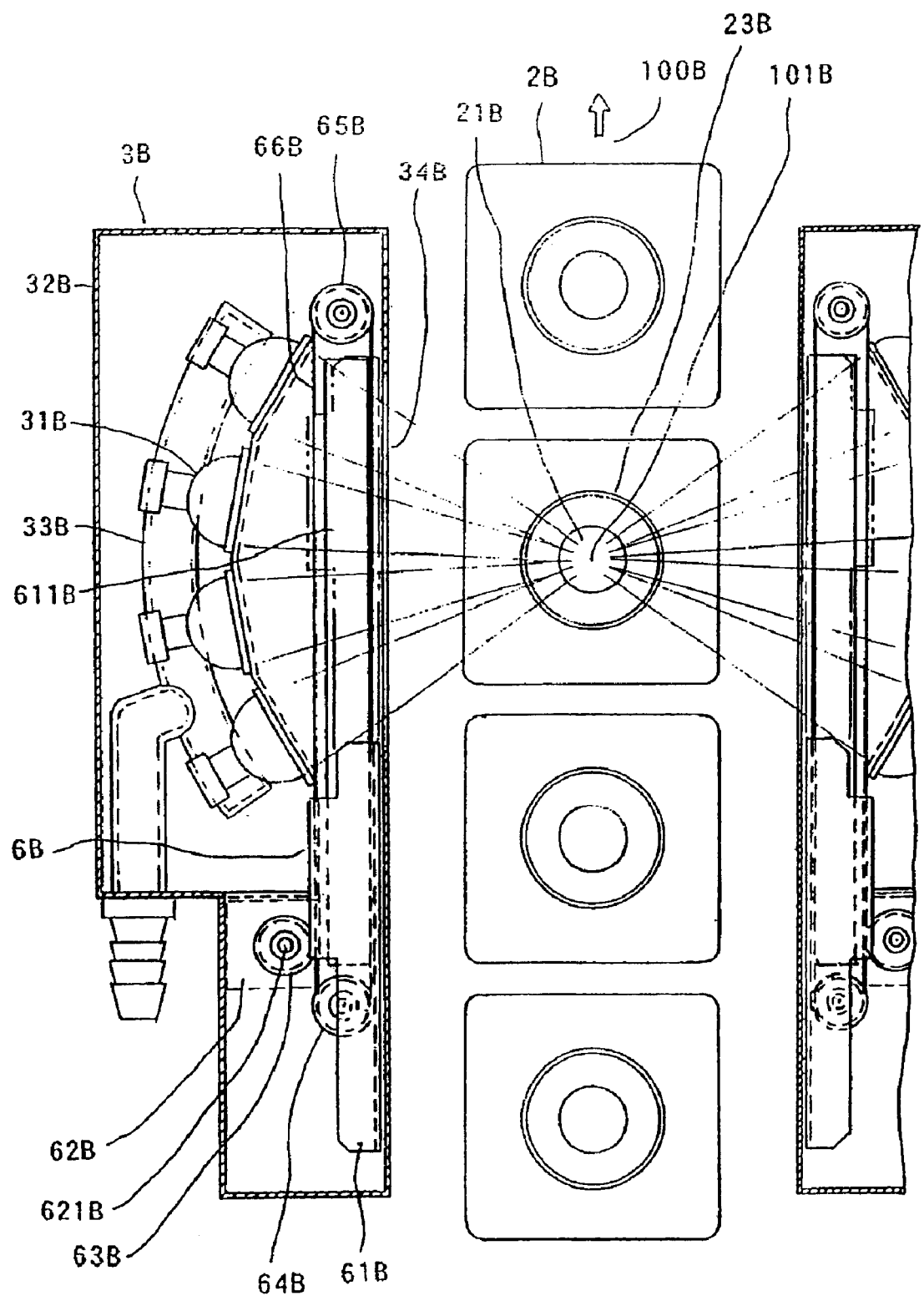
FIG. 8 is a plan view showing the essential parts of the second embodiment shown in FIG. 7.

As shown in FIGS. 7 and 8, a light projecting window 34B is formed in front of each of lamp boxes 32B to project beams of light toward the inspecting position 101B.

A light blocking device 6B is provided at a part of each of the lamp boxes 32B. The light blocking device 6B includes a light blocking shutter 61B which is arranged to close or open the light projecting window 34B. The light blocking shutter 61B is mounted on a linear slide rail 611B at its upper part and is thus arranged to be slidable forward and backward in parallel with the transport conveyer 1B and in the traveling direction of the receiving tray 2B.

At each lamp box 32B, the light blocking shutter 61B is arranged to be slid by a forward and backward rotating motor 62B which is provided with brake means. A drive pulley 63B is mounted on the shaft 621B of the motor 62B. A head pulley 64B and a tension pulley 65B are disposed at two ends of the sliding movement. A wire rope 66B is stretched by wrapping it round the pulleys 64B and 65B. A part of the light blocking shutter 61B is connected to the wire rope 66B. When the motor 62B with brake means is rotated forward and backward, the light blocking shutter is pulled by the wire rope 66B to make a reciprocal motion under the guidance of the linear slide rail 611B. The light projecting window 34B is then closed and opened accordingly.

More specifically, the light projecting window 34B is open when the light blocking shutter 61B is on the side of the head pulley 64B. When the motor 62B rotates, the light blocking shutter 61B is pulled and moved by the wire rope 66B toward the tension pulley 65B to close the light projecting window 34B. The light blocking shutter 61B comes to a stop where the light projecting window 34B is completely closed. The motor 62B is provided preferably with such a brake that is capable of instantly causing the motor 62B to reversely rotate.

The condenser lens 41B of the light receiving means 4B is arranged in the same manner as the condenser lens 41 of the first embodiment. Therefore, the details of the condenser lens 41B are omitted from description.

A combining mount part 40B is arranged to combine the condenser lens 41B with a spectrometer 7B by adjusting the focal point of the condenser lens 41B to the position of a slit 71B provided in the spectrometer 7B. A light reducing filter mounting plate 43B and a light receiving shutter 44B are disposed in a position where the light transmitted through the object of inspection is converged and stopped down toward the slit 7B with a dark room formed to encompass these parts.

Since the light reducing filter mounting plate 43B is arranged in the same manner as in the first embodiment, the details of it are omitted from description.

Figure 9:
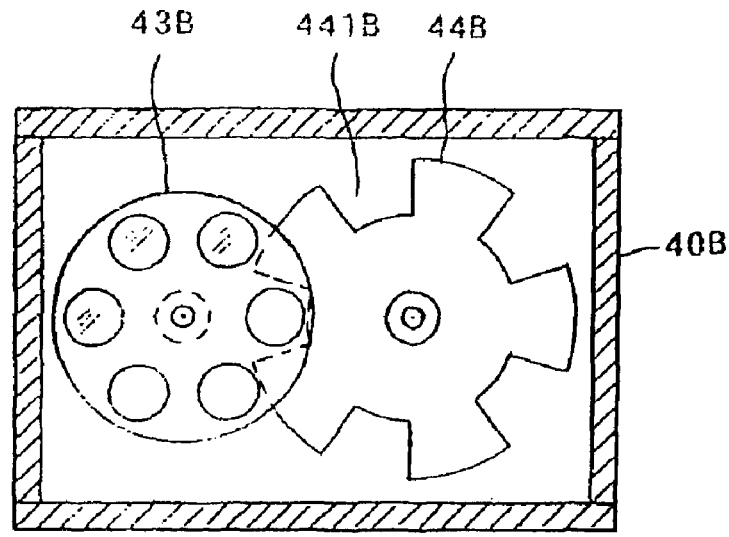
FIG. 9 is a sectional view taken along a line C—C of FIG. 7 to show a light reducing filter and a light receiving shutter as in an open state.
Figure 10:
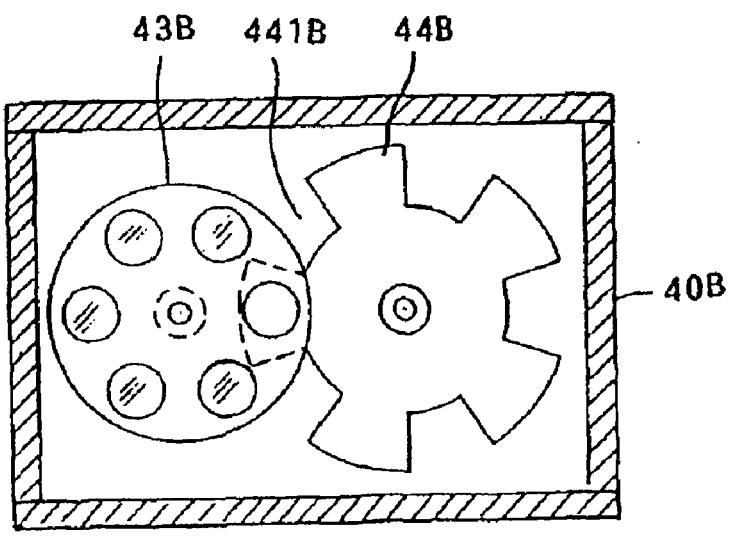
FIG. 10 is a sectional view of the same part as FIG. 9 showing the light receiving shutter as in a closed state.

The light receiving shutter 44B is disposed preferably close to the light reducing filter mounting plate 43B. As shown in FIGS. 9 and 10, the shutter 44B is formed by cutting away the periphery of a disk into a plurality of cutaway parts 441B which are evenly spaced. The shutter 44B is thus arranged to open and close a light receiving optical path 400B in front of the slit 71B.

A stepping drive device 442B is arranged to drive in an inching manner the light receiving shutter 44B to move and come to a stop at a predetermined position every time a receiving tray 2B comes with the inspecting object F placed thereon. The light receiving shutter 44B is thus arranged to open (FIG. 9) to allow the transmission light from the object F to pass the entrance (incident) slit 71B of the spectrometer 7B when the center part of the receiving tray 2B comes to pass the inspecting position 101B with the object F placed thereon.

The shutter 44B closes (FIG. 10) when the center part of the receiving tray 2B is not at the inspecting position 101B while it is conveyed.

With the light receiving shutter 44B arranged in this manner, the influence of any current accumulated during the last process of inspection can be eliminated from an output value of the transmission light currently obtained by detecting the zero level (dark current) of the light receiving circuit of the spectrometer. The internal qualities inspection can be carried on without any error by virtue of this arrangement.

The spectrometer 7B is arranged to have the light incident on the entrance slit 71B reflected by a known grading mirror 72B, to receive the reflected light by a linear array sensor 73B and to photoelectrically convert the light thus received.

White level calibrating means 5B is mounted on an upper frame 17B which is disposed above the inspecting position 101B.

A linear motion driving type motor 54B incorporating therein a rack-and-pinion arrangement is arranged on the upper frame 17B to move a shaft 53B up and down. A calibrating plate mounting part 50B is mounted on the lower end of the shaft 53B.

A white level calibrating plate 51B is mounted on the calibrating plate mounting part 50B with a retaining metal 52B. In carrying out a calibrating operation, the linear motion drive type motor 54B is caused to rotate forward and backward to vertically move the shaft 53B in such a way as to move the white level calibrating plate 51B downward near to the upper surface of the receiving tray 2B or to retract it upward.

The retaining metal 52B is formed to cover the receiving tray 2B by extending it wider than the upper surface of the receiving tray 2B to prevent the projected light of the lamps from directly coming into a space between it and the upper surface of the receiving tray 2B and by bending it downward on both the right and left sides on which the light projecting means is arranged.

When the receiving tray 2B is detected to be carrying the inspecting object F (an agricultural product) thereon by a sensor provided for a preceding process before the inspecting position 101B, the white level calibrating plate 51B is retracted upward.

INDUSTRIAL APPLICABILITY

According to this invention, as described in the foregoing, with the receiving tray conveyed by the conveyer, the inspecting object is lightly fitted on the receiving tray in such a way as to cover the upper part of the transmission light passage which vertically penetrates the center of a receiving seat provided on the receiving tray. In other words, the transmission light passage is blocked by the object to prevent external light and the beams of projected light at the inspecting position. Therefore, even a slight quantity of transmission light can be detected by the condenser lens which is set upward below the transport path of the receiving tray.

The internal qualities such as a sugar forming degree and acidity of an agricultural product to be inspected is uneven and fluctuates according to its sunny side and its shadowy sides. The agricultural product also might have a denatured part or a scar. However, the beams of projected light comes out from the transmission light passage after passing through a wide range of various parts of the agricultural product to give reliable information on the internal qualities.

The transmission light obtained from the transmission light passage which is shielded from external light is converged and subjected to spectral analysis. By this, internal qualities data averaged for each inspecting object can be obtained. The objects inspected in this manner can be accurately sorted by quality on the basis of the data.

Since many light projecting lamps are arranged to project light in a concentrative manner, the invented system can use compact lamps each of which has a relatively small output. This arrangement lowers the amount of heat generation and lengthens the service lives of the lamps. The invented system is, therefore, applicable to a consolidated shipping station or sorting-and-packaging facilities which are continuously operating over a long period of time.

In the internal qualities inspection system arranged according to an aspect of this invention, the transmission light converged by the condenser lens is arranged to be led to the spectrometer by means of optical fiber. In this case, the spectrometer can be set away from a part immediately below the receiving tray transport path. In the case of a compact transport conveyer having a relatively small space below the transport path, therefore, the condenser lens of the system can be combined with a spectrometer which is arranged in a large size to enhance its performance for spectral analysis.

The internal qualities inspection system according to another aspect of this invention is arranged to have the condenser lens combined with the spectrometer in one unified body without using any optical fiber. Compared with the case where the optical fiber is used, since no attenuation loss of the transmission light is caused by the optical fiber before the transmission light reaches the spectrometer, a better efficiency can be attained. The system of this type is therefore applicable to cases where the space below the receiving tray transport path of the transport conveyer is relatively large or where the inspecting object is an agricultural product having a relatively thick skin and thus gives a less quantity of transmission light.

The internal qualities inspection system arranged according to a further aspect of the invention is provided with means for selectively inserting light reducing filters of varied kinds in the light receiving path between the spectrometer and the condenser lens which converges the light transmitted through the object of inspection. Therefore, even in cases where the transmissible quantity of light varies with the kind of the object of inspection, the quantity of light coming into the spectrometer can be adjusted by the selective use of the light reducing filters. The use of the light reducing filters permits the amplification factor of the operational amplifier of the spectrometer to be preset on the basis of an inspecting object of such a kind that has a less transmissible quantity of light.

When the inspecting object is switched from an object having a relatively small transmissible light quantity over to an object having a relatively large transmissible light quality such as a tomato, for example, the transmitted light is reduced through one of the light reducing filters before the transmitted light comes into the spectrometer, so that the spectral analysis can be carried out without the fear of overflow of the operational amplifier. The system, therefore, can be used for inspecting the objects of many kinds.

The internal qualities inspection system arranged according to yet another aspect of this invention is provided with the light receiving shutter. The shutter is arranged to open and close the passage of light in the light receiving optical path provided between the condenser lens and the spectrometer every time one receiving tray passes with an inspecting object placed thereon. Since the shutter is arranged to allow no light to come into the spectrometer when the receiving tray is empty or when the inspection is not performed, the inside of the spectrometer and an amplifying circuit can be prevented from being affected by a temperature increase and the like.

The system is applicable to such cases where a space available below the lower face of the receiving tray is too narrow for forming any lower light blocking face on the outside of a transmission light exit.

In the internal qualities inspection system arranged according to still another aspect of the invention, the light converging part of the light receiving means is provided with the lens hood for securing a visual field on the object side of the condenser and dust proof means for removing dust by blowing air at the outer surface of the front glass of the lens hood. The arrangement enables the condenser lens to converge the transmission light without any hindrance within the visual field as all dirt and dust accumulating within the visual field of the condenser lens is blown away even though the condenser lens is arranged to face upward from below the receiving trays while they are consecutively conveyed one after another.

In the internal qualities inspection system arranged according to a still further aspect of the invention, the white level calibrating plate is arranged to be moved back and forth to cover the receiving seats of the receiving trays being conveyed one after another by the transport conveyer. This arrangement permits calibration to be automatically carried out when more than a predetermined number of empty receiving trays are passing consecutively even while the system is in operation. Therefore, a calibrating action on the overall output value of the system necessary for spectral analysis due to variations of environment temperature or deterioration of the optical system taking place during the lapse of operation time can be automatically carried out at the time of a start, a break, a temporary suspension of operation, or the like. The spectral analysis thus can be stably and reliably carried on over a long period of time.

In the internal qualities inspection system arranged according to yet another aspect of the invention, the light reducing filters of different light reducing rates are selectively used in combination with increasing or decreasing a number of light projecting lamps to be lighted up in cases where the transmissible quantity of light of the inspecting objects slightly vary with the kind of them. Therefore, spectral analysis can be carried out by adjusting the transmission light to an optimum quantity for the operational amplifier, so that the internal qualities inspection can be reliably made.

Further, the internal qualities inspection system according to yet a further aspect of this invention is provided with light blocking device for blocking the beams of light projected by the light projecting lamps in front of the lamp box. By using this device, the adverse effects of heat of light projection, such as deformation, denaturing, etc. can be prevented, as no light is projected on the receiving tray, without putting out the light projecting lamps which are alight.

The environment conditions for light emission by the light projecting lamps vary to make the beams of light unstable and to eventually cause the inspection accuracy to become unstable every time the lamps are put out and lighted up again. This problem, however, can be solved by leaving the lamps alight to keep the projected light stable with this light blocking device actuated. The use of this device enables the system to operate again at the same level of inspection accuracy as before after a break or temporary suspension of its inspecting operation.

In accordance with this invention described above, an internal qualities inspection system can be arranged to be most apposite to conveyers arranged to sort agricultural products or the like by quality.

While the foregoing description and drawings represent the present invention, it will be obvious to those skilled in the art that various changes may be made therein without departing from the true spirit and scope of the present invention.

What is claimed is:

1. A two-side multiple lamp online inner quality inspection system comprising:
   transport means for continuously running and conveying objects of inspection one by one by placing each of the objects on a receiving tray;
   a transmission light passage being formed in the receiving tray to vertically penetrate the center part thereof and a light blocking receiving seat being arranged at the upper part of said transmission light passage in an annular shape to elastically engage the object in a tight contact therewith;
   light projecting means for projecting beams of light on the object from lateral direction both left and right by using a plurality of light projecting lamps at a predetermined position of said transport means;
   light receiving means arranged to converge and receive as transmission light the projected beams of light coming through the inside of the object of inspection and passing downwardly through the transmission light passage of the receiving tray; light projected;
   means for making spectral analysis on said transmission light received, said transport means extending underneath the receiving tray, which runs through the transport path, and which is arranged to be able to locate the light receiving means fixed closely underneath the receiving tray running through the inspecting position;

said light projecting means having a large number of light projecting lamps set in a lamp box and arranged on both the right and left sides of a transport path to concentratedly project a light from lateral direction on the object on said receiving tray at an inspecting position from different positions and at different angles in such a way as to cover a wide area of said object ranging from an obliquely front part to an obliquely rear part on each of the right and left sides of the object;

said light receiving means having a condenser lens with dust-proof means arranged upwardly below said receiving tray to converge transmission light coming through said transmission light passage which vertically penetrate said receiving tray, and a combining mount part forming a dark room through said condenser lens and a mount part to lead the transmission light to the spectrometer, and which is arranged to have the light entrance plane of an optical fiber at the focal point in said combining mount part to lead the transmission light converged by the optical fiber to said spectrometer.

2. A system according to claim 1, wherein said combining mount part of said light receiving means is arranged to have the light entrance plane of an optical fiber at the focal point of said condenser lens and to lead the converged transmission light to said spectrometer through said optical fiber.

3. A system according to claim 1, wherein said combining mount part of said light receiving means is arranged to have the focal point of said condenser lens coincide with an entrance slit of said spectrometer.

4. A system according to claim 1, wherein the quantity of light coming into said spectrometer is arranged to be reducible by arranging means for selectively inserting light reducing filters of varied kinds in a light receiving optical path provided at said combining mount part between said condenser lens and said spectrometer.

5. A system according to claim 1, wherein a transmission light shutter is arranged in said light receiving optical path of said combining mount part between said condenser lens and said spectrometer to block the passing of the transmission light every time one receiving tray passes with the object of inspection placed thereon; and said shutter is actuated to open when the transmission light passage of said receiving tray is on the visual field of said condenser lens and to close when the transmission light passage comes outside of the visual field, so that no light is allowed to come into said spectrometer when no inspecting operation is performed.

6. A two-side multiple lamp online inner quality inspection system comprising:

transport means for conveying objects of inspection one by one by placing each of the objects on a receiving tray;

a receiving tray in which a transmission light passage is formed to vertically penetrate the center part thereof and a light blocking receiving seat being arranged at the upper part of said transmission light passage in an annular shape to elastically engage the object in a tight contact therewith;

light projecting means for projecting beams of light on the object by using a plurality of light projecting lamps at a predetermined position of said transport means;

light receiving means arranged to converge and receive as transmission light, from underneath the receiving tray, the projected beams of light coming through the inside of the object of inspection and passing downwardly through the transmission light passage of the receiving tray; means for making spectral analysis on said transmission light received, said light receiving means having an air blow hole arranged to blow an air from lateral direction toward the center of upper surface of light receiving window of lens hood of condenser lens located upwardly underneath the receiving tray, and which is arranged to proof upper surface of the condense lens from dust by generating an air flow from upper surface of the light receiving window toward the outside direction.

7. A system according to claim 1, further comprising a white-level calibrating plate moving mechanism which is arranged to retractably move a white level calibrating plate forward to cover the receiving seat of said receiving tray from outside of the transport path of said receiving tray when no inspecting object is on said receiving tray at the inspecting position where said light projecting means and said light receiving means arc disposed, and wherein calibration can be automatically carried out by moving said white level calibrating plate forward to cover said receiving seat of said receiving tray when a predetermined number of empty receiving trays pass the inspecting position.

8. A system according to claim 1, further comprising means for increasing or decreasing the quantity of light projected by said large number of light projecting lamps of said projecting means by increasing or decreasing a number of light projecting lamps to be lighted up among said large number of light projecting lamps according to the size of the inspecting object or the light transmissible degree of the inspecting object which vary with the kind of the inspecting object.

9. A system according to claim 1, wherein said light projecting means includes a lamp box for mounting the plurality of light projecting lamps on both right and left sides of the transport path, and the projecting window of the lamb box is arranged to concentratedly project a light on the object on the receiving tray at an inspecting position ranging from an obliquely front part to an obliquely rear part on each of the right and left sides of the object, and having a light blocking shutter at said projecting window to make and break thereof to block light from being projected on the object with the light of lamp on.

10. A system according to claim 6, wherein said light projecting means includes a lamp box for mounting the plurality of light projecting lamps on both right and left sides of the transport path, and the projecting window of the lamb box is arranged to concentratedly project a light on the object on the receiving tray at an inspecting position ranging from an obliquely front part to an obliquely rear part on each of the right and left sides of the object, and having a light blocking shutter at said projecting window to make and break thereof to block light from being projected on the object with the light of lamp on.

11. A two-side multiple lamp online inner quality inspection system comprising:

transport mean for conveying objects of inspection one by one by placing each of the objects on a receiving tray, a transmission light passage being formed in the receiving tray to vertically penetrate the center part thereof and a light blocking receiving seat being arranged at the upper part of said transmission light passage in an annular shape to elastically engage the object in a tight contact therewith;

light projecting means for projecting beams of light on the object by using a plurality of light projecting lamps at a predetermined position of said transport means;

light receiving means arranged to converge and receive transmission light coming through the inside of the object of inspection with the beams of light projected;

means for making spectral analysis on said transmission light received, said light projecting means having a large number of light projecting lamps arranged on both the right and left sides of a transport path to concentratedly project on the object on said receiving tray at an inspecting position from different positions and at different angles in such a way as to cover a wide area of said object ranging from an obliquely front part to an obliquely rear part on each of the right and left sides of the object;

said light receiving means having a condenser lens arranged below said receiving tray to converge transmission light coming through said transmission light passage which vertically penetrate said receiving tray and a spectrometer arranged in combination with said condenser lens through a combining mount part which is arranged to lead converged transmission light to said spectrometer;

wherein said condenser lens is provided with a lens hood which is arranged to secure a visual field on the object side of said condenser lens and a light receiving window which is made of transparent glass and disposed on the front side of said lens hood to form a dust-proof structure; and dust-proof means is arranged on the outside of said transparent glass to blow air from the periphery thereof toward the center of said light receiving window.

12. A two-side multiple lamp online inner quality inspection system comprising:

transport mean for conveying objects of inspection one by one by placing each of the objects on a receiving tray;

a transmission light passage being formed in the receiving tray to vertically penetrate the center part thereof and a light blocking receiving seat being arranged at the upper part of said transmission light passage in an annular shape to elastically engage the object in a tight contact therewith;

light projecting means for projecting beams of light on the object by using a plurality of light projecting lamps at a predetermined position of said transport means;

light receiving means arranged to converge and receive transmission light coming through the inside of the object of inspection with the beams of light projected;

means for making spectral analysis on said transmission light received, said light projecting means having a large number of light projecting lamps arranged on both the right and left sides of a transport path to concentratedly project on the object on said receiving tray at an inspecting position from different positions and at different angles in such a way as to cover a wide area of said object ranging from an obliquely front part to an obliquely rear part on each of the right and left sides of the object;

said light receiving means having a condenser lens arranged below said receiving tray to converge transmission light coming through said transmission light passage which vertically penetrate said receiving tray and a spectrometer arranged in combination with said condenser lens through a combining mount which is arranged to lead converged transmission light to said spectrometer;

means for increasing or decreasing the quantity of light projected by said large number of light projecting means by increasing or decreasing a number of light projecting lamps to be lighted up among said large number of light projecting lamps according to the size of the inspecting object or the light transmissible degree of the inspecting object which vary with the kind of the inspecting object.

* * * * *